United States Patent [19]

Collins

[11] Patent Number: 5,295,946
[45] Date of Patent: Mar. 22, 1994

[54] EXTERNAL PENILE ERECTION DEVICE

[75] Inventor: Moseley Collins, West Palm Beach, Fla.

[73] Assignee: Gemini Medical Corporation, West Palm Beach, Fla.

[21] Appl. No.: 978,490

[22] Filed: Nov. 18, 1992

[51] Int. Cl.[5] ............................................. A61F 5/41
[52] U.S. Cl. ....................................................... 600/41
[58] Field of Search ............................ 600/38, 39, 41; 606/202; 128/DIG. 20

[56] References Cited

U.S. PATENT DOCUMENTS

| | | | |
|---|---|---|---|
| 3,759,253 | 9/1973 | Cray | 128/79 |
| 4,407,275 | 10/1983 | Schroeder | 600/38 |
| 4,539,980 | 9/1985 | Chaney | 128/79 |
| 4,641,638 | 2/1987 | Perry | 600/39 |
| 5,085,209 | 2/1992 | Gottschalk | 600/41 |

*Primary Examiner*—Cary E. O'Connor
*Attorney, Agent, or Firm*—Alvin S. Blum

[57] ABSTRACT

A device for affecting or enhancing erection of the penis comprises an external inflatable cuff which encircles the shaft of the penis at its base and extends distally. The cuff is provided with a plurality of volume expandable annular spaces arranged parallel to one another. The spaces are filled with fluid under pressure from a squeeze bulb to affect a tourniquet action. The spaces are inflated sequentially in a proximal to distal direction. As the spaces become sequentially pressurized, the inner diameter of the cuff is reduced, constricting the penis and trapping blood within the shaft and forcing it distally to thereby increase the rigidity of the penis.

1 Claim, 1 Drawing Sheet

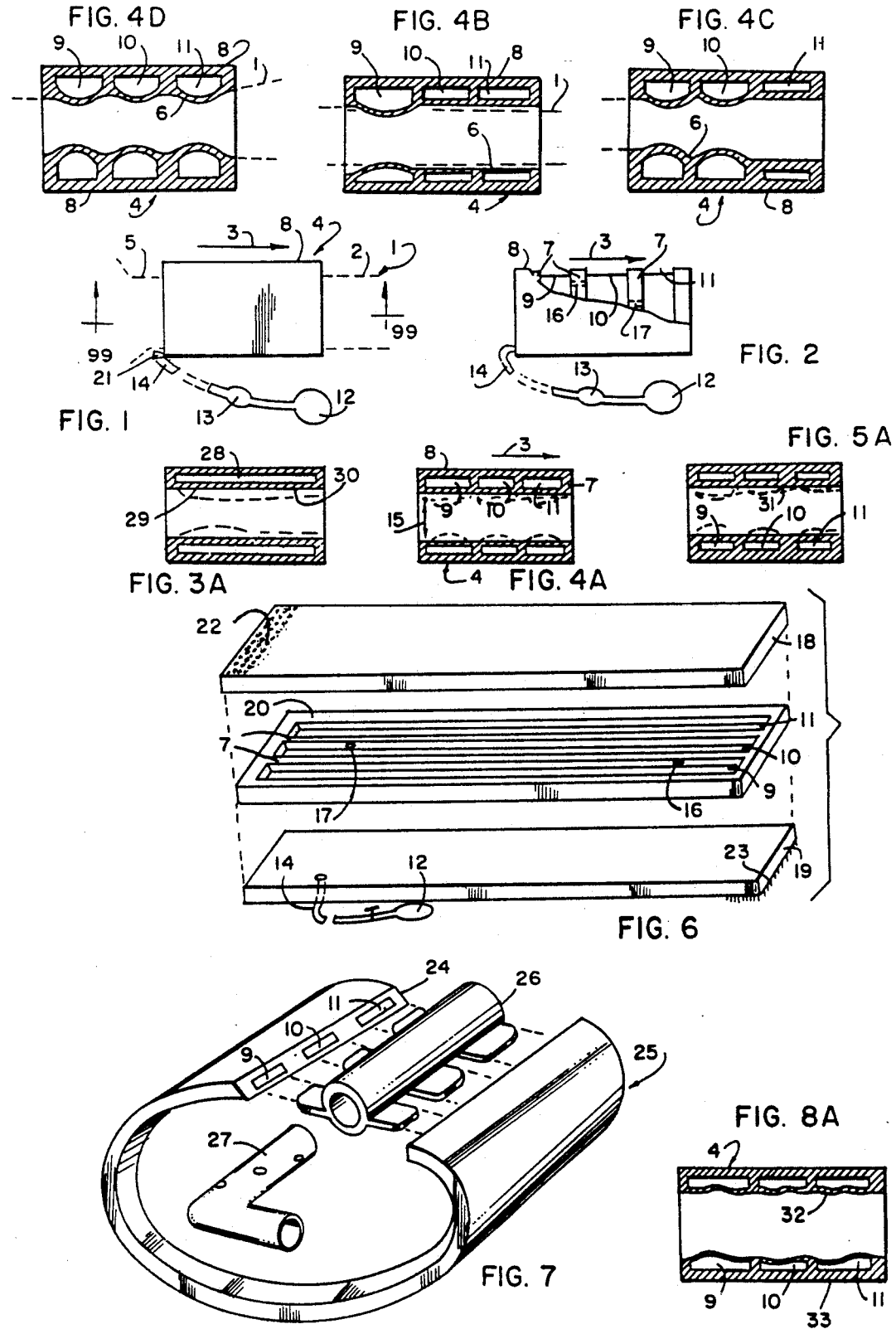

EXTERNAL PENILE ERECTION DEVICE

BACKGROUND OF THE INVENTION

This invention relates to devices for overcoming male impotence and more particularly to a device applied externally to the shaft of the penis that inflates to constrict the shaft to enhance rigidity.

With advancing age, and also in certain pathological conditions, men may not be able to achieve an erection with sufficient rigidity for satisfactory coitis. Various devices of the prior art for overcoming the problem are surgically implanted within the penis. Some are permanently rigid and hinged. Others provide a flaccid inflatable chamber which becomes rigid when inflated with fluid. The inflating apparatus is also implanted within the body. These invasive procedures destroy normal tissue, they are attended by the usual surgical risks, such as infection and hemorrhage, and they are not always successful. There is little chance of restoring normal function when they are removed.

There is no way to temporarily try the devices to predict success following the operation. It is devastating to go through the expense, trauma, and risk of an irreversible procedure and then find out that it does not improve function. It is also discouraging to the physician to deal with the dissatisfied patient for whom he has recommended the procedure. Non surgical treatments includes use of a vacuum chamber to expand the penis followed by a constrive cuff at the base.

THE PHYSIOLOGY OF PHYSICAL IMPOTENCE

The penis shaft is made up of three cylindrical masses of erectile tissue covered by skin. The erectile tissue masses are composed of large venous sinusoids or spaces which are fed by blood from arteries and drained by veins. They contain very little blood when not aroused. When aroused, the arteries pump extra blood to the tissue and the penis enlarges. The veins draining the sinusoids are equiped with constrictor muscle to block off venous drainage during arousal. This causes the sinusoids to engorge with blood at arterial pressure. The inflated erectile tissue expands to fill the skin of the penis tightly, resulting in an enlarged and rigid organ.

In many cases of impotence, there is adequate arterial blood supply, but apparently inadequate closing off of the venous channels to inflate the sinusoids to maintain satisfactory rigidity or erection.

SUMMARY OF THE INVENTION

It is accordingly an object of the invention to provide a temporary, non-invasive, inexpensive device to overcome impotence that is completely under the control of the user. It is another object to provide such a device that will readily fit a user regardless of the size of the organ. It is yet another object that the device be safe and harmless and not disturbing to the user or his female partner.

The device of the invention comprises an inflatable cuff means which completely encircle the shaft of the penis at its proximal portion near the pubic bone. The cuff has a substantial length, extending distally toward the glans a distance preferably of thirty-three to fifty millimeters. The cuff is inflated with fluid by a squeeze bulb with either liquid or gas. The outer wall of the cuff does not stretch readily so that its diameter remains unchanged by inflation. The inner wall, adjacent the penis, expands during inflation so that its diameter decreases until it compresses the shaft of the penis, obstructing the venous drainage thereof. This causes the venous sinusoids to engorge with blood, causing an erection.

The entire inner wall does not expand uniformly during inflation. The device is so constructed that the proximal portion of the cuff, i.e. the portion closest to the body, expands first. Then, after the venous return is blocked, the inflation of the cuff and constriction of the shaft advances distally until the entire cuff is inflated and forced tightly against the shaft. This action forces the trapped blood into a smaller portion of the shaft, further expanding the sinusoids and enhancing rigidity. The penis is hard and capable of normal coitis with the device in place with normal sensations. It is not ordinarily felt by the female.

When fluid pressure is released by the user, the cuff deflates, and the penis becomes flaccid. The device is removed for later reuse. It causes no permanent changes to the penis. If it is not successful, no harm has been done. Ordinarily, the user must be sexually aroused by massage, foreplay, or by use of a vacuum chamber before inflating the cuff for successful operation. The inflatable cuff is a sequentially activated tourniquet which constricts the shaft progressively along the proximal to distal axis.

These and other objects, advantages and features of the invention will become more apparent when the detailed description is studied in conjunction with the drawings, in which:

BRIEF DESCRIPTION OF THE DRAWINGS

FIG. 1 is a side elevation view of a device of the invention.

FIG. 2 is a side elevation view, partially broken away, of a device of the invention.

FIG. 3A is a sectional view taken on line 99—99 of FIG. 1.

FIG. 4A is a sectional view taken on line 99—99 of FIG. 1 with another internal structure in uninflated condition.

FIG. 4B is a sectional view of the device of FIG. 4A in one-third inflated condition.

FIG. 4C is a sectional view of the device of FIG. 4A in two-thirds inflated condition.

FIG. 4D is a sectional view of the device of FIG. 4A in fully inflated condition.

FIG. 5A is a sectional view taken on line 99—99 of FIG. 1 with another internal structure.

FIG. 6 is an exploded perspective view of the device of FIG. 2.

FIG. 7 is an exploded perspective view of another embodiment of the invention.

FIG. 8A is a view as in FIG. 4A of an embodiment with a non-resilient inner surface layer.

DETAILED DESCRIPTION OF PREFERRED EMBODIMENTS

Referring now first to FIGS. 1, 2 and 4A, B, C and D, a penis 1 is shown in phantom with a shaft 2 and arrow 3 indicating the proximal to distal axis and the inflatable penile erection device 4 of the invention enclosing the shaft 2 at its base 5. The device 4 is comprised of an inner circumferential surface layer 6 of a thin, resilient, stretchy material. Surrounding the inner surface layer are a series of parallel spacer bands 7, and surrounding the spacer bands is an outer, less stretchy, circumferential surface layer 8 which together define three parallel annular expandable spaces 9, 10, 11. An inflating bulb 12 and valve 13 are connected through tube 14 to the first space 9. Squeezing the bulb forces fluid, either liquid such as water or gas such as air, into the first space 9 under pressure causing the space to expand. The inner circumferential surface layer being thinner and more stretchable than the outer circumferential surface layer, it stretches inward, reducing the inside diameter 15 which is forced against the penile shaft at its base 5, thereby constricting the venous return from the penis and trapping blood therein as shown in FIG. 4B. A narrow first channel 16 provides a fluid communication between space 9 and space 10. After space 9 is expanded fluid moves through channel 16 into space 10 which expands as it fills as shown in FIG. 4C. When space 10 is filled, pressure builds up and fluid moves from space 10 through a second channel 17 into space 11 which then fills and expands as shown in FIG. 4D. As spaces 10 and 11 expand sequentially and distally in the direction of arrow 3 along the proximal to distal axis, the shaft is further compressed, causing the trapped blood to be forced distally along the shaft, increasing the turgor and rigidity of the penis. The device may be constructed from a series of endless bands cemented together. The tube 14 may be provided with a quick-disconnect fitting 21 to remove tube and bulb after inflation for more comfortable use.

FIG. 6 illustrates another embodiment in which three rectangular strips are joined together, a thin, resilient, stretchy, inner strip 18, a thick, non-stretchy, outer strip 19, and a spacer strip 20 sandwiched between the two which provides the partitions 7, dividing the assembly into three parallel expandable spaces 9, 10 and 11. Fastening means 22 and 23 at the opposite ends of the assembled strip provide means for joining the two ends together after the device is wrapped around the penis. This permits adjustment to organs of different diameters. The fastening means may be hook and loop fasteners, adhesives or other means well known in the art. The bulb 12 and tube 14 are connected to the first expandable space 9, with channels 16 and 17 for sequentially filling the second and third parallel channels as described above.

FIG. 7 shows another embodiment of the invention in which an extruded three channel tube 24, preferably molded of a thermoplastic elastomer, is formed into a circular band 25 with connector 26 providing selective access to the three expandable channels 9, 10 and 11 via rotation of valve plug 27 which is provided with fluid under pressure through a pressure bulb and tube as shown above. With this system, the valve connects the pressurizing fluid first to space 9 until it is expanded. The plug 27 is rotated until space 9 is sealed and space 10 is connected to the fluid source until it is expanded. The plug is then rotated until space 10 is also sealed and space 11 is connected. After the space 11 is expanded, the plug is again rotated to seal space 11 also, to produce effective erection of the penis. FIG. 3A shows an embodiment in which a single expandable space 28 is provided with an inner stretchable circumferential surface which is thinner and more stretchable at its proximal end 29 and becomes thicker and progressively less stretchable toward the distal end 30 thereof. As shown in phantom, the inner diameter becomes reduced progressively from proximal to distal end of the cuff as the inner surface layer stretches under the force of the inflating fluid.

Referring now to FIG. 5A, an embodiment is shown in which three expandable spaces 9, 10 and 11 are provided with increasing thickness of the resilient inner layer 31 from proximal to distal ends of the cuff. When the spaces are pressurized simultaneously, space 9 will expand first, followed by space 10 and then space 11.

The device is typically formed of a soft, resilient, stretchable elastic material having a durometer of 30 and a 2000 P.S.I. tensile strength such as natural rubber, silicone rubber, polyurethane or thermoplastic elastomer.

Referring now to FIG. 8 an embodiment is shown in which the inner layer 32 as well as well as the outer layer 33 is made of a non-stretchable material such as polyester providing a flaccid inner surface layer with enlarged spaces 9, 10, 11. When not pressurized, these spaces are readily collapsed as shown. The fluid transfer means is arranged to pressurize the three spaces sequentially, along the proximal to distal axis as shown, for example, in FIG. 7.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A penile erection device for external application to the shaft of a penis, the device comprising:
   an inflatable cuff means for completely encircling a shaft of a penis at the penile base, said cuff means, when positioned on a penile shaft, extending along a proximal to distal axis of said shaft, and having at least one volume expandable annular space defined by an outer circumferential surface layer and an inner circumferential surface layer;
   said outer circumferential surface layer being substantially fixed and forming a substantially unchangeable outer diameter and said inner circumferential surface layer being changable and forming an inner diameter which is varied by changing the volume of said at least one volume expandable annular space and constriction circumferential pressure is thereby applied to said shaft as said space is expanded;
   means for inflating said at least one volume expandable annular space in a sequential manner along said proximal to distal axis, whereby said shaft is first constricted proximally and then progressively constricted distally to thereby enhance rigidity of said shaft,
      in which said cuff means includes a plurality of separate volume expandable annular spaces arranged parallel to one another along said proximal to distal axis and said inner circumferential surface layer is formed of a resilient stretchable material the thickness thereof increasing along said proximal to distal axis; and
   said means for inflating is connected to all said annular spaces at once, whereby said spaces will expand in sequence axially due to the first enhanced stretching of the thinner inner circumferential surface layer.

* * * * *